US 6,628,975 B1

(12) United States Patent
Fein et al.

(10) Patent No.: US 6,628,975 B1
(45) Date of Patent: Sep. 30, 2003

(54) OXIMETER SENSOR WITH DIGITAL MEMORY STORING DATA

(75) Inventors: Michael E. Fein, deceased, late of Mountain View, CA (US), by Marcia Fein, executrix; Paul D. Mannheimer, Danville, CA (US); Rodney Chin, Oakland, CA (US); Adnan Merchant, Fremont, CA (US)

(73) Assignee: Mallinckrodt Inc., Hazelwood, MO (US)

( * ) Notice: Subject to any disclaimer, the term of this patent is extended or adjusted under 35 U.S.C. 154(b) by 2 days.

(21) Appl. No.: 09/943,823

(22) Filed: Aug. 30, 2001

Related U.S. Application Data
(60) Provisional application No. 60/229,616, filed on Aug. 31, 2001.

(51) Int. Cl.$^7$ .................................................. A61B 5/00
(52) U.S. Cl. ....................................... 600/323; 600/331
(58) Field of Search ............................... 600/309–310, 600/322–326, 331, 334

(56) References Cited

U.S. PATENT DOCUMENTS

| 3,720,199 A | 3/1973 | Rishton et al. |
| 3,790,910 A | 2/1974 | McCormack |
| 4,303,984 A | 12/1981 | Houvig |
| 4,446,715 A | 5/1984 | Bailey |
| 4,621,643 A | 11/1986 | New, Jr. et al. |
| 4,684,245 A | 8/1987 | Goldring |
| 4,700,708 A | 10/1987 | New, Jr. et al. |
| 4,717,080 A | 1/1988 | Sauer |
| 4,734,873 A | 3/1988 | Malloy et al. |
| 4,845,649 A | 7/1989 | Eckardt et al. |
| 4,858,615 A | 8/1989 | Meinema |
| 4,862,872 A | 9/1989 | Yabe et al. |
| 4,913,150 A * | 4/1990 | Cheung et al. ............. 600/323 |
| 4,942,877 A | 7/1990 | Sakai et al. |
| 5,007,423 A * | 4/1991 | Branstetter et al. ......... 600/334 |
| 5,008,843 A | 4/1991 | Poelsler et al. |
| 5,016,198 A | 5/1991 | Schreiber |
| 5,058,588 A | 10/1991 | Kaestle |
| 5,070,732 A | 12/1991 | Duncan et al. |
| 5,162,725 A | 11/1992 | Hodson et al. |
| 5,246,003 A | 9/1993 | DeLonzor |
| 5,259,381 A | 11/1993 | Cheung et al. |

(List continued on next page.)

FOREIGN PATENT DOCUMENTS

| WO | WO93/06776 | 4/1993 |
| WO | WO97/29678 | 8/1997 |

*Primary Examiner*—Eric F. Winakur
*Assistant Examiner*—Matthew Kremer

(57) ABSTRACT

The present invention provides a memory chip for use in an oximeter sensor, or an associated adapter or connector circuit. The memory chip allows the storing of different data to provide enhanced capabilities for the oximeter sensor. In addition to providing unique data to store in such a memory, the invention describes unique uses of data stored in such a memory. The data stored in the memory chip includes information relating to enhancing the performance of the oximetry system.

3 Claims, 1 Drawing Sheet

U.S. PATENT DOCUMENTS

| | | | |
|---|---|---|---|
| 5,347,476 A | 9/1994 | McBean, Sr. | |
| 5,365,462 A | 11/1994 | McBean, Sr. | |
| 5,371,128 A | 12/1994 | Ulman et al. | |
| 5,425,375 A | 6/1995 | Chin et al. | |
| 5,429,129 A | 7/1995 | Lovejoy et al. | |
| 5,443,801 A | 8/1995 | Langford | |
| 5,528,519 A | 6/1996 | Ohkura et al. | |
| 5,645,059 A | 7/1997 | Fein et al. | |
| 5,660,163 A | 8/1997 | Schulman et al. | |
| 5,720,293 A * | 2/1998 | Quinn et al. | 600/505 |
| 5,758,644 A | 6/1998 | Diab et al. | |
| 5,800,350 A | 9/1998 | Coppleson et al. | |
| 5,830,121 A | 11/1998 | Enomoto et al. | |
| 5,855,609 A | 1/1999 | Knapp | |
| 5,987,343 A * | 11/1999 | Kinast | 600/323 |
| 6,044,283 A | 3/2000 | Fein et al. | |
| 6,104,938 A | 8/2000 | Huiku et al. | |
| 6,122,536 A | 9/2000 | Sun et al. | |
| 6,241,679 B1 | 6/2001 | Curran | |
| 6,298,255 B1 | 10/2001 | Cordero et al. | |
| 6,308,089 B1 | 10/2001 | von der Ruhr et al. | |
| 6,356,774 B1 * | 3/2002 | Bernstein et al. | 600/323 |
| 6,360,114 B1 | 3/2002 | Diab et al. | |
| 6,377,829 B1 | 4/2002 | Al-Ali | |
| 6,405,087 B1 | 6/2002 | Snell | |
| 6,463,310 B1 * | 10/2002 | Swedlow et al. | 600/323 |
| 6,466,808 B1 * | 10/2002 | Chin et al. | 600/323 |

* cited by examiner

OXIMETER SENSOR WITH DIGITAL MEMORY STORING DATA

CROSS-REFERENCES TO RELATED APPLICATIONS

This application claims priority to U.S. Provisional Patent Application No. 60/229,616, filed Aug. 31, 2001, which is hereby incorporated by reference herein.

BACKGROUND OF THE INVENTION

The present invention relates to oximetry sensors and, in particular, pulse oximetry sensors which include coded information relating to characteristics of the sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

An encoding mechanism is shown in U.S. Pat. No. 4,700,708, the disclosure of which is incorporated herein by reference. This mechanism relates to an optical oximeter probe which uses a pair of light emitting diodes (LEDs) to direct light through blood-perfused tissue, with a detector picking up light which has not been absorbed by the tissue. The operation depends upon knowing the wavelength of the LEDs. Since the wavelength of LEDs can vary, a coding resistor is placed in the probe with the value of the resistor corresponding to the actual wavelength of at least one of the LEDs. When the oximeter instrument is turned on, it first applies a current to the coding resistor and measures the voltage to determine the value of the resistor and thus the value of the wavelength of the LED in the probe.

U.S. Pat. No. 5,259,381 recognizes that the coded value of the wavelength of the red LED provided by a coding resistor may be inaccurate, since the actual wavelength can vary with temperature. Accordingly, this patent teaches including a temperature sensor in the oximeter probe to measure the actual temperature. With the actual temperature, and the coded wavelength value, a look-up table can be consulted to determine the actual LED wavelength for that temperature.

Another method of storing coded information regarding the characteristics of the LEDs is shown in U.S. Pat. No. 4,942,877 assigned to Minolta. This patent discloses using an EPROM memory to store digital information, which can be provided in parallel or serially from the sensor probe to the remote oximeter. The memory is described as storing coefficients for the saturation equation, wavelength, sub-wavelength (where 2 peaks for LED), half-width of wavelength spectrum emitted by LED, intensity of LEDS or ratio, and on time of LEDS (written by the processor).

Other examples of coding probe characteristics exist in other areas. Multiple calibration values are sometimes required, with this making the circuitry more complex or requiring many leads. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another probe with digital characterization information stored in a PROM, which is read serially using a shift register.

Typically, the coding element is mounted in the probe itself. For instance, U.S. Pat. No. 4,621,643 shows the coding resistor mounted in the probe element itself. In addition, U.S. Pat. No. 5,246,003 shows the coding resistor being formed with a printed conductive material on the probe itself.

In some devices, an electrical connector coupled by a cable to a device attached to a patient may include a coding element. For example, U.S. Pat. No. 3,720,199 shows an intra-aortic balloon catheter with a connector between the catheter and a console. The connector includes a resistor with a value chosen to reflect the volumetric displacement of the particular balloon. U.S. Pat. No. 4,684,245 discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

U.S. Pat. No. 5,645,059 teaches using a modulated signal to provide the coded data to a remote analyzer. U.S. Pat. No. 5,429,129 shows using a voltage regulator to produce a specific voltage value in response to an attempt to read by the analyzer.

Hewlett-Packard Company U.S. Pat. No. 5,058,588 teaches an oximeter sensor with an encoding element that could be resistor, ROM, or customized integrated circuit. The encoding element encodes the type of sensor (in particular, type indicating area of placement on body—finger, ear, foot, arm; also, the type of sensor can indicate transmission/reflection type, or adult/neonate {indicating correction to be performed on theoretical oxygen saturation, allow switching between physiological limits such as minimum/maximum pulse rates for adults/neonates}; the maximum driving current may be adapted according to type of sensor, and contact of sensor with tissue can be tested by means of an attenuation measurement if sensor type is known).

Nellcor U.S. Pat. No. 5,645,059, the disclosure of which is hereby incorporated herein by reference, teaches coding information in sensor memory used to provide pulse modulated signal, to indicate the type of sensor (finger, nose), the wavelength of a second LED, the number of LEDs, the numerical correction terms to the standard curves, and an identifier of the manufacturer.

A number of catheter patents also discuss encoding information in the catheter. Sentron U.S. Pat. No. 4,858,615 teaches encoding the type of sensor, type number, serial number, date of production, safe use life of the sensor, correction data for non-linearity, pressure sensitivity, offset, and temperature sensitivity.

Interflo Medical Published PCT Application No. PCT/US92/08263, Publication No. WO 93/06776 teaches encoding patient specific data, size, manufacture date, batch number, sterilization date, expiration date, transducer number and type, manufacturer's name and address, thermistor heating element resistance, filament efficiency, program segments or patient historical data., format version for the calibration data, trademark information, catheter unique serial number, ship date, other date and time information, security code to identify manufacturer, thermal mass, filament composition, coefficient of resistance, layout byte, checksum, copyright, number of seconds since a certain date, patient weight, patient height, timestamp of 1st CO data point, and a count of all CO data points in EEPROM.

Dulex-Ohmeda of Boulder, Col. markets an oximeter sensor product that encodes data into resistor values representing pointers to a lookup table containing coefficients (as in U.S. Pat. No. 4,700,708) as well as indicating a range of LED drive current to use with the sensor. The LEDs are driven with a higher or lower drive currents depending upon the value of the resistor in a particular sensor.

Honeywell U.S. Pat. No. 4,303,984 (expires Dec. 14, 1999) describes a memory which stores characterization information, such as linearization information for a pressure sensor. Alnor Instrument U.S. Pat. No. 5,162,725 describes storing both calibration and ID information in a sensor memory. Seimans U.S. Pat. No. 5,016,198 describes a coding memory in a sensor with data for defining sensor's characteristic curve. McBean U.S. Pat. No. 5,365,462 describes a date code in a sensor memory. Honeywell U.S. Pat. No. 4,734,873 describes a pressure sensor with a PROM storing coefficients for a polynomial. Robert Bosch U.S. Pat. No. 4,845,649 describes a PROM in a sensor storing correcting data.

McBean U.S. Pat. No. 5,371,128 relates to EEPROM in sensor with sensor type code and calibration data. McBean U.S. Pat. No. 5,347,476 describes an accuracy code. Otax U.S. Pat. No. 5,528,519 shows a PROM in a connector for oximeter.

Square D Company U.S. Pat. No. 5,070,732 shows calibration data in a sensor memory. Baxter U.S. Pat. No. 5,720,293 talks about different calibration information for a catheter, including a security code (encryption is discussed), serial number, model number, ID data such as calibration, manufacture, sterilization and ship date or other date and time information, a software program segment, security code for identifying whether sensor made by same manufacturer as monitor manufacturer, filament or transducer resistance, heat transfer coefficient, thermal mass, filament composition and coefficient of resistance, layout byte, copyright notice, checksum, random data bytes. Porsche U.S. Pat. No. 5,008,843 describes a sensor with EEPROM ID and characteristics data.

BRIEF SUMMARY OF THE INVENTION

The present invention provides a memory chip for use in an oximeter sensor, or an associated adapter or connector circuit. The memory chip allows the storing of different data to provide enhanced capabilities for the oximeter sensor. In addition to providing unique data to store in such a memory, the invention describes unique uses of data stored in such a memory. The data stored in the memory chip includes information relating to enhancing the performance of the oximetry system.

DETAILED DESCRIPTION OF THE INVENTION

Figure 1:
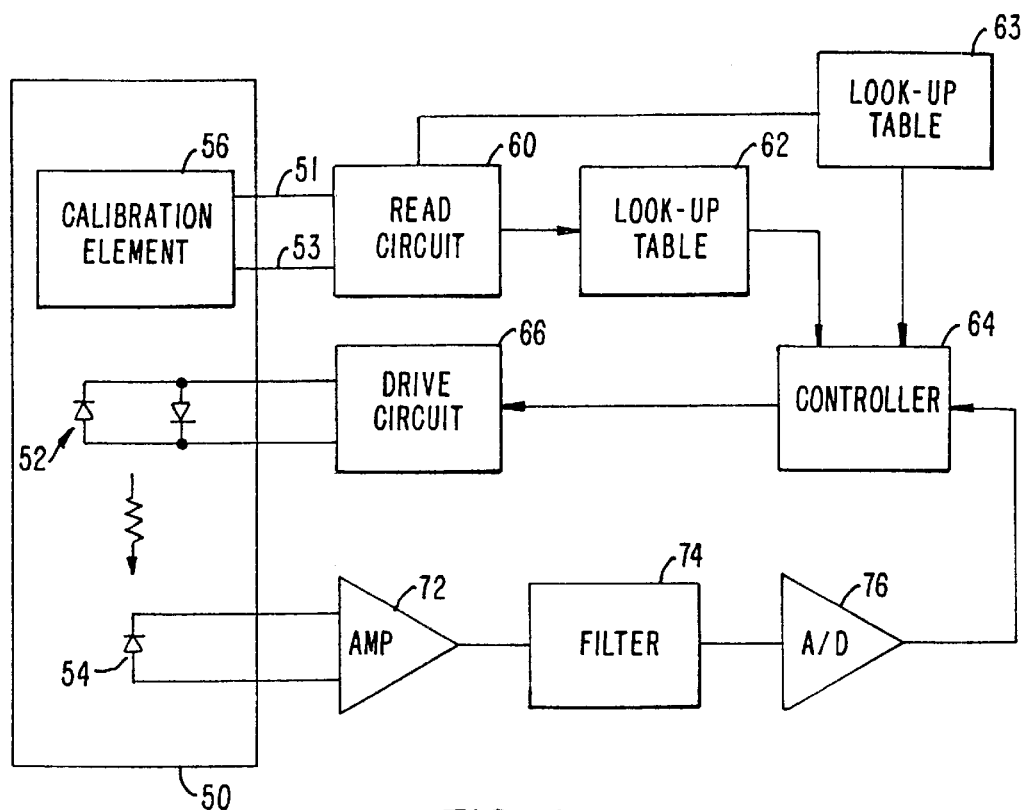
FIG. 1 is a block diagram of a pulse oximeter system in accordance with the present invention.

FIG. 1 is a block diagram of a pulse oximeter system incorporating a calibration memory element 56 according to the invention. In one embodiment, memory element 56 is a two-lead semiconductor digital memory chip. The calibration element is part of the sensor 50 which also includes red and infrared LEDs 52 as in the prior art, along with a detector 54. If desired, LEDs 52 may be replaced with other light emitting elements such as lasers.

The oximeter includes read circuit 60, drive circuit 66, look-up tables 62 and 63, controller 64, amplifier 72, filter 74, and analog-to-digital converter 76. Read circuit 60 is provided for reading multiple coded values across the two leads 51, 53 connected to calibration element 56. One value is provided to a look-up table 62 to determine appropriate wavelength dependent coefficients for the oxygen saturation calculation, as in the prior art. The other value(s) are then provided to another look up table(s) 63 which provides input (e.g., coefficients) to other calculations performed by controller 64. These additional calculations may enhance the performance and/or safety of the system. Controller 64 provides signals to a drive circuit 66, to control the amount of drive current provided to LEDs 52. Memory 56 may, for example, be implemented as a random access memory (RAM), a FLASH memory, a programmable read only memory (PROM), an electrically erasable PROM, a similar programmable and/or erasable memory, any kind of erasable memory, a write once memory, or other memory technologies capable of write operations.

As in the prior art, detector 54 is connected through an amplifier 72 and a filter 74 to an A/D converter 76. This forms a feedback path used by controller 64 to adjust the drive current to optimize the intensity range of the signal received. For proper operation the signal must be within the analog range of the circuits employed. The signal should also be well within the range of A/D converter 76 (e.g., one rule that may be applied is to adjust LED drives and amplifier gains so that both red and IR signals fall between 40% and 80% of full scale reading of converter 76). This requires correct and independent settings for both the red and infrared LEDs.

Numerous types of data can be stored in memory chip 56. Some of these types of data are now discussed.

Temperature at Which to Switch to Motion-Signal Algorithm

The motion-signal algorithm here refers to the sensors designed to be used where "motion provides the signal", i.e., the cardiac pulse need not be present or discernible in order for the oximeter to provide $SP0_2$ values. Instead, the red and IR waveforms resulting from the motion itself are used for determining the arterial saturation (see e.g., U.S. Pat. No. 6,018,673). This feature is possible for tissue beds that are well "arterialized" (a large supply of arterial blood relative to the metabolic needs of the tissue) resulting in a small aterio-venous saturation difference, as well as other signal characteristics that are not germane to this discussion. We have observed that the necessary degree of arterialization correlates well to being "well perfused" at the tissue site, which itself correlates well to the tissue bed being warm. Thus by monitoring the temperature of the skin at the sensor site, and by knowing a value of temperature (programmed into the memory chip) at which the "motion-signal" algorithm can be utilized for the specific sensor design being used, improved reading accuracy through motion can be better accomplished.

Information on Use of Pins

Chemical Sensor for EtO Cycles

An electro-chemical or thermal device that senses and stores to memory the number of exposures (zero, once, or potentially more than once or the actual number) to sterilization cycles could be used to capture the history of the sensor. Excessive exposure to sterilization cycles degrades a number of components in the sensor, and can affect its performance. A sensor exceeding a certain number of exposures could cause a display to indicate the sensor needs to be replaced.

Changeable Key

Data encryption utilizes private and/or public keys to scramble the data written to the memory chip and later decipher the data so that only authorized devices are supported. To further prevent the use with a monitor that isn't certified to provide correct results, the sensor manufacturing system could periodically change the private and/or public keys. The change in the key could be communicated to the instrument via the memory chip in encrypted form. The purpose of this feature is to elevate the level of security in the memory system.

Accelerometer on Chip

This might be used in a scheme in which the memory chip was on the bandage, not in the connector. This combines a MEMS accelerometer with any of several different chips that might usefully be placed in the sensor head; local digitizing chip, preamp chip, memory chip.

Accelerometer data may be used to warn of the presence of motion (in which case special algorithms may be called into play or oximetry may be suspended), or actually to help correct for motion (to the extent to which we can produce algorithms which can predict physio-optic effects of known motion).

Optical Shunt

The amount of optical shunting could be measured for each sensor, or family of sensors. The value would be stored in the sensory memory for the monitor to read and use to adjust the processing coefficients.

Monitor Ambient Temperature

This might be used, e.g., in overseeing the operation of an actively warmed sensor (i.e., a sensor provided with a low-power heating or warming surface). There is preferably a thermal cutout in the control system of actively warmed sensors, that causes operation to terminate if the sensor goes over a certain temperature. This is a necessary component of protecting the patient against burns. If the reason for a high sensor temperature is that the environment is warm, it could be quite acceptable to continue oximetry, even though warmer operation would be shut down. In the absence of knowledge about environmental temperature, a high temperature reading might have to be assumed to mean that something was wrong with the sensor, in which case ALL operation might have to cease. An environmental temperature sensor in the plug could help to tell which rule to apply.

The memory chip could record the calibration of the device used for thermometry.

RCAL Resistance Built Into Chip

In legacy oximetry sensors there is a resistor which is selected and installed in the sensor connector, to correspond to the wavelength of the red LED, as described in U.S. Pat. No. 4,700,708. The wavelength difference from LED to LED has an impact on the calibration of the saturation measurement, if not compensated for. Oximeters designed for such sensors will read the value of resistance and adjust its calculation accordingly.

When adding the memory chip, memory compatible oximeters will be able to obtain the necessary calibration coefficients from the memory chip but the legacy instruments will still need a calibration resistor value. With a resistance properly built-in to the chip and trimmed or selected at sensor manufacture, only one device would need to be installed in the sensor connector. That would reduce the overall-cost, yet keep the sensor compatible with both the legacy instruments and the new memory compatible instruments.

Encode Contact Resistance

When making measurements of the resistance that is placed in the sensor, for calibration information purposes, one of the factors that can influence that measurement is the contact resistance of the connectors that are between the oximeter and the resistor itself. In order to compensate for connectors that are significant in their impact on the measure, one could encode the contact resistance of the connector and subtract that algorithmically from the measured resistance to get a more accurate measurement of the resistance of the calibration resistor. This would enhance the accuracy with which the resistance measurement is made and therefore make the instrument less prone to miscalculation and therefore inaccuracies in maturation calculation and display.

Measure Capacitance to Balance Common Mode Rejection

One of the interfering noise sources that can have an effect on oximetry is that of common mode electrical noise. This can come from the surrounding electrical environment. Other instruments, lights, drills etc. can produce electrical fields that can couple into the cable between the patient and the oximeter. Once coupled-in, they can make measurements more difficult, less accurate or not possible, depending on the severity of the noise. To help reduce this common mode noise, differential amplifiers are used for amplifying the signal from the sensor. These amplifiers amplify only the difference between two signal wires. Thus, if the common mode signal is coupled exactly the same into both wires, the amplifier will not amplify it because the same signal is present on both wires.

If the two wires have different coupling to their electrical environment then they will present different signals and the difference will be amplified as if it were a signal. One component that influences this coupling is the capacitance of the lines to the outside world. This is affected by the manufacture of the cable, materials, twists in the wire, etc. If one measures the cable during manufacture and then stores that information in the memory chip, it can be read when the oximeter is operating. Once the capacitance for the two wires to the shield are known the instrument can be provided with a tunable capacitance device that balances the two lines and makes the noise coupling to the lines better matched. This reduces the amount of susceptibility to the external noise that becomes coupled into the patient cable. Reduced noise results in better measurements or the ability to make measurements on some patients at all.

Active Ambient Light Measurement

Another potential source of interference with pulse oximetry sensors is the interference caused by ambient light in the environment reaching the sensor's photodetector. This can be made worse when a sensor comes loose or the ambient light is extremely high in value. By characterizing the sensor during manufacture or by its design one can know the level of ambient light that can be tolerated, and give a warning to the operator when the level has been exceeded. An external measure of ambient light by the pulse oximeter monitor provides operators the opportunity to adjust the sensor, the light, or both to effect an improvement in the performance of the oximeter. This can be accomplished, e.g., with a photodetector positioned on or near the pulse oximeter.

Active Pressure Adjustment for Modulation Enhancement

The stronger the pulsatile signal the better the chances are of measuring the saturation accurately. One way to enhance the modulation percentage is to apply pressure in the range of the median pulsatile pressure or the mean arterial pressure. When implemented, one can use relatively low cost transducers and supply calibration coefficients in the memory to allow accurate pressure readings to be made. The memory can also contain the pressure settings and/or expected modulation enhancement capability to determine effectiveness of the pressure enhancement.

Measure Sensor Wetness

A moisture sensor or impedance sensor can detect the amount of wetness of the sensor. This can be used for different purposes, and can be stored in the sensor memory for trending or monitoring.
  a) To determine sensor malfunction (e.g., Oxicliq). The sensor can be disabled if the wetness exceeds a threshold, which could be stored in the sensor memory.
  b) Patient isolation. Some sensors may not provide for isolation of the patient from the electronics for excessive wetness. The maximum allowable wetness could be stored in the sensor memory.

Display for Additional Wavelengths (More Than 2)

The memory can store information about what parameters are to be analyzed and displayed when the extra wavelengths are used in the pulse oximeter sensor. Oxygen saturation may be displayed when 2 wavelengths are used, while additional information could be displayed when an extra wavelength or more are used (Hct, COHb, etc.)

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiments disclosed, but that the invention will include all embodiments and equivalents falling within the scope of the claims.

What is claimed is:

1. A method for operating an oximeter sensor, the method comprising:
    emitting light from a light emitting element;
    detecting light at a light detecting element;
    reading digital data that is stored in a memory device on the sensor, wherein the digital data includes capacitance values of wires coupled between the oximeter sensor and an oximeter monitor;
    tuning capacitances of the wires using the capacitance values to balance the capacitances of the wires so that noise signals on the wires are more closely matched; and
    amplifying signals from the sensor received on the wires using a differential amplifier.

2. Method of claim 1 wherein reading the digital data that is stored in the memory device further comprises:
    reading digital data from the memory device including a temperature value; and wherein the method further comprises:
        determining arterial oxygen saturation using a motion-signal algorithm when a temperature at a patient's skin reaches the temperature value.

3. Method of claim 1 wherein reading the digital data that is stored in the memory device further comprises:
    reading digital data from the memory device including a temperature threshold value; and the method further comprises:
        terminating operation of the oximeter sensor if a temperature of the sensor increases above the temperature threshold value.

* * * * *

UNITED STATES PATENT AND TRADEMARK OFFICE
CERTIFICATE OF CORRECTION

PATENT NO. : 6,628,975 B1
DATED : September 30, 2003
INVENTOR(S) : Michael E. Fein et al.

It is certified that error appears in the above-identified patent and that said Letters Patent is hereby corrected as shown below:

<u>Title page,</u>
Insert Item -- [60] Provisional application No. 60/229,616, filed on Aug. 31, 2000. --

Signed and Sealed this

Twenty-second Day of March, 2005

JON W. DUDAS
*Director of the United States Patent and Trademark Office*